US012580111B1

(12) United States Patent
Mourran et al.

(10) Patent No.: US 12,580,111 B1
(45) Date of Patent: Mar. 17, 2026

(54) CORROSION-RESISTANT PERMANENT MAGNET AND INTRAVASCULAR BLOOD PUMP COMPRISING THE MAGNET

(71) Applicant: Abiomed Europe GmbH, Aachen (DE)

(72) Inventors: Claudia Mourran, Aachen (DE); Thorsten Siess, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 407 days.

(21) Appl. No.: 17/969,190

(22) Filed: Oct. 19, 2022

Related U.S. Application Data

(62) Division of application No. 17/052,904, filed as application No. PCT/EP2019/059968 on Apr. 17, 2019, now Pat. No. 11,569,015.

(30) Foreign Application Priority Data

May 8, 2018 (EP) .................................... 18171245

(51) Int. Cl.
*H01F 7/02* (2006.01)
*A61M 60/148* (2021.01)
(Continued)

(52) U.S. Cl.
CPC ........... *H01F 7/021* (2013.01); *A61M 60/148* (2021.01); *A61M 60/17* (2021.01);
(Continued)

(58) Field of Classification Search
CPC .... H01F 7/021; H01F 41/026; A61M 60/148; A61M 60/17; A61M 60/216;
(Continued)

(56) References Cited

U.S. PATENT DOCUMENTS

| | | | |
|---|---|---|---|
| 4,063,971 | A | 12/1977 | Greinacher et al. |
| 4,863,805 | A | 9/1989 | Suzuki et al. |

(Continued)

FOREIGN PATENT DOCUMENTS

| | | | |
|---|---|---|---|
| EP | 3319098 A1 | 5/2018 | |
| JP | 10341703 A | 2/1991 | |

(Continued)

OTHER PUBLICATIONS

Japanese Office Action for Application No. JP2024-015142 mailed Dec. 3, 2024, 7 pgs.

(Continued)

*Primary Examiner* — Ricardo D Morales
(74) *Attorney, Agent, or Firm* — Botos Churchill IP Law LLP

(57) ABSTRACT

This invention is directed to a corrosion-resistant permanent magnet, to a method for producing a corrosion-resistant permanent magnet, and to an intravascular blood pump comprising the magnet. The magnet is corrosion resistant due to a composite coating comprising a first layer structure and optionally a second layer structure on the first layer structure, each layer structure comprising an inorganic layer, a linker layer on the inorganic layer, and an organic layer formed from poly(2-chloro-p-xylylene) on the linker layer. The inorganic layers comprise aluminum and/or aluminum oxide.

20 Claims, 3 Drawing Sheets

(51) Int. Cl.

| | |
|---|---|
| ***A61M 60/17*** | (2021.01) |
| ***A61M 60/216*** | (2021.01) |
| ***A61M 60/419*** | (2021.01) |
| ***A61M 60/422*** | (2021.01) |
| ***A61M 60/818*** | (2021.01) |
| ***A61M 60/829*** | (2021.01) |
| ***C23C 14/16*** | (2006.01) |
| ***C23C 14/32*** | (2006.01) |
| ***C23C 16/40*** | (2006.01) |
| ***C23C 16/455*** | (2006.01) |
| ***H01F 41/02*** | (2006.01) |

(52) U.S. Cl.

CPC ........ *A61M 60/216* (2021.01); *A61M 60/419* (2021.01); *A61M 60/422* (2021.01); *A61M 60/818* (2021.01); *A61M 60/829* (2021.01); *C23C 14/16* (2013.01); *C23C 14/325* (2013.01); *C23C 16/403* (2013.01); *C23C 16/45555* (2013.01); *H01F 41/026* (2013.01)

(58) Field of Classification Search

CPC .............. A61M 60/419; A61M 60/422; A61M 60/818; A61M 60/829; C23C 14/16; C23C 14/325; C23C 16/403; C23C 16/45555

See application file for complete search history.

(56) References Cited

U.S. PATENT DOCUMENTS

| | | | |
|---|---|---|---|
| 5,154,978 | A | 10/1992 | Nakayama et al. |
| 6,240,320 | B1 | 5/2001 | Spehr et al. |
| 9,775,974 | B2 | 10/2017 | Leung et al. |
| 2002/0148237 | A1 | 10/2002 | Thiesen et al. |
| 2003/0041920 | A1 | 3/2003 | Hoshi et al. |
| 2004/0264521 | A1 | 12/2004 | Ness et al. |
| 2005/0239220 | A1 | 10/2005 | Dauwalter et al. |
| 2005/0261544 | A1 | 11/2005 | Gan |
| 2006/0122456 | A1 | 6/2006 | Larose et al. |
| 2006/0245959 | A1 | 11/2006 | Larose et al. |
| 2007/0280841 | A1 | 12/2007 | Larose et al. |
| 2008/0185173 | A1 | 8/2008 | Bedinger et al. |
| 2008/0200750 | A1 | 8/2008 | James |
| 2011/0039050 | A1 | 2/2011 | Hogg et al. |
| 2011/0207328 | A1 | 8/2011 | Speakman |
| 2012/0035411 | A1 | 2/2012 | Larose et al. |
| 2015/0142949 | A1 | 5/2015 | Nair |
| 2015/0235763 | A1 | 8/2015 | Dempsey et al. |
| 2016/0088756 | A1 | 3/2016 | Ramadas |
| 2016/0240309 | A1* | 8/2016 | Jia ......................... H01F 41/026 |
| 2016/0308405 | A1 | 10/2016 | Thompson et al. |
| 2017/0040605 | A1 | 2/2017 | Hwang et al. |
| 2017/0056631 | A1 | 3/2017 | Leung et al. |
| 2017/0084372 | A1 | 3/2017 | Sassaman et al. |
| 2017/0174506 | A1 | 6/2017 | Gianchandani et al. |
| 2018/0289877 | A1 | 10/2018 | Schumacher et al. |
| 2018/0335037 | A1 | 11/2018 | Shambaugh et al. |
| 2019/0275225 | A1 | 9/2019 | Brown |
| 2019/0311850 | A1 | 10/2019 | Siess et al. |
| 2021/0067137 | A1 | 3/2021 | Green et al. |

FOREIGN PATENT DOCUMENTS

| | | | |
|---|---|---|---|
| JP | H07170064 | A | 7/1995 |
| JP | H09289108 | A | 11/1997 |
| JP | H10290138 | A | 10/1998 |
| JP | 2000256878 | A | 9/2000 |
| JP | 2005210095 | A | 8/2005 |
| JP | 2006351946 | A | 12/2006 |
| JP | 2010518627 | A | 5/2010 |
| JP | 2012119338 | A | 6/2012 |
| JP | 2013255792 | A | 12/2013 |
| JP | 2018504215 | A | 2/2018 |
| JP | 7402044 | B2 | 12/2023 |
| WO | 0206562 | A1 | 1/2002 |
| WO | 2006060260 | A2 | 6/2006 |
| WO | 2017129933 | A1 | 8/2017 |

OTHER PUBLICATIONS

Office Action from corresponding Japanese Patent Application No. 2020-562698 dated Mar. 28, 2023 (9 pp.).

Office Action from corresponding European Application No. 19718687.7-1212 dated Jul. 3, 2022 (9 pp.).

Office Action from corresponding Indian Application No. 202037046874 dated Aug. 31, 2022 (6 pages).

International Search Report and Written Opinion for corresponding International Application No. PCT/EP2019/059968 dated Jul. 4, 2019 (11 pages).

Office Action for corresponding CN Application No. 201980031228.8 dated Jun. 17, 2022 with English Translation (15 pages).

Kianzong Xie, Atomic Layer Deposited Aluminum Oxide and Parylene C Bi-Layer Encapsulation for Biomedical Implantable Devices, PhD Dissertation, Department of Electrical and Computing Engineering, The University of Utah, Dec. 2013 (Year: 2013).

Office Action for Korean Application No. 10-2020-7035356 dated Mar. 14, 2024, 14 pps.

* cited by examiner

CORROSION-RESISTANT PERMANENT MAGNET AND INTRAVASCULAR BLOOD PUMP COMPRISING THE MAGNET

CROSS-REFERENCE TO RELATED APPLICATIONS

The present application is a divisional of U.S. patent application Ser. No. 17/052,904, filed Nov. 4, 2020, now allowed, which is a national phase entry under 35 U.S.C. § 371 of International Application No. PCT/EP2019/059968 filed Apr. 17, 2019, published as International Publication No. WO 2019/214920 A1, which claims priority from European Patent Application No. 18171245.6 filed May 8, 2018, the disclosures of all of which are hereby incorporated herein by reference.

BACKGROUND OF THE INVENTION

This invention relates to corrosion protection of permanent magnets. In particular, this invention relates to permanent magnets having a protective coating rendering the magnets resistant to corrosion, and to methods for producing corrosion-resistant permanent magnets. This invention also relates to intravascular blood pumps comprising the inventive corrosion-resistant permanent magnets. While the invention is applicable to all kinds of permanent magnets, rare-earth permanent magnets are preferred, and neodymium iron boron (NdFeB) permanent magnets are particularly preferred.

BRIEF SUMMARY OF THE INVENTION

Intravascular blood pumps support blood flow in a patient's blood vessel. They are inserted percutaneously into, for example, the femoral artery and guided through the body's vascular system to their destination, for example a ventricle of the heart.

A blood pump typically comprises a pump casing having a blood flow inlet and a blood flow outlet. In order to cause a blood flow from the blood flow inlet to the blood flow outlet, an impeller or rotor is rotatably supported within the pump casing about an axis of rotation, with the impeller being provided with one or more blades for conveying blood.

An exemplary blood pump is illustrated in FIG. 1. FIG. 1 is a schematic longitudinal section of an exemplary intravascular blood pump 10. The blood pump has a motor section 11 and a pump section 12 which are disposed coaxially one behind the other and result in a rod-shaped construction form. The pump section is extended by a flexible suction hose (not shown) which has, at its end and/or in its side wall, openings for the entry of blood to the pump. The end of the blood pump 10 facing away from the suction hose is connected to a catheter 14, optionally in combination with a guide wire for steering the blood pump to its destination.

The exemplary intravascular blood pump shown in FIG. 1 has the motor section 11 and the pump section 12 firmly connected to one another. The motor section 11 has an elongate housing 20 in which the electric motor 21 is housed. An electric motor has a rotor and a stator. The stator is the stationary part of the motor's electromagnetic circuit, while the rotor is the moving part. Either the rotor or the stator comprises electrically conductive windings, while the other comprises permanent magnets. Electric current flowing in the windings creates an electromagnetic field interacting with the magnetic field of the permanent magnets to generate the forces that turn the rotor. In the exemplary blood pump of FIG. 1, the stator 24 of the electric motor 21 has, in the usual way, numerous circumferentially distributed windings as well as a magnetic return path 28 in the longitudinal direction. It is firmly connected to the motor housing. The stator 24 surrounds the rotor 1 connected to the motor shaft 25 and consisting of a permanent magnet magnetized in the active direction. The motor shaft 25 extends over the total length of the motor housing 20 and protrudes distally out of the latter. There, it carries an impeller 34 with blades 36 projecting therefrom or pump blades which rotate within a tubular pump housing 32 which in turn is firmly connected to the motor housing 20.

The proximal end of the motor housing 20 has the flexible catheter 14 sealingly attached thereto. In the present disclosure "proximal" and "distal" indicate the position with respect to a physician inserting the intravascular blood pump, i.e. the distal end is at the impeller side. Through the catheter 14 there extend electrical cables 23 for power supply to and control of the electric motor 21. There additionally extends through the catheter 14 a purge-fluid line 29 which penetrates the proximal end wall 22 of the motor housing 20. Purge fluid (schematically illustrated by bold arrows) is fed through the purge-fluid line 29 into the interior of the motor housing 20, flows through clearance 26 between the rotor 1 and the stator 24, and exits through the end face 30 at the distal end of the motor housing. The purging pressure is chosen such that it is higher than the blood pressure present, in order to thereby prevent blood from penetrating into the motor housing. Depending on the case of application, the pressure of the purge fluid is between 300 and 1400 mmHg at the motor where the pressure is built up.

Well suited as a purge fluid is a fluid having a viscosity higher than the viscosity of water ($\eta$=0.75 mPa·s at 37° C.), in particular a purge fluid having a viscosity at 37° C. of 1.2 mPa's or higher. For example, a solution of 5% to 40% glucose in water for injection can be used, but physiological saline solution is also suitable.

Upon rotation of the impeller 34, blood (schematically illustrated by unfilled arrows) is sucked through the end face suction opening 37 of the pump housing 32 and conveyed backward within the pump housing 32 in the axial direction. Through outlet openings 38 of the pump housing 32, the blood flows out of the pump section 12 and further along the motor housing 20. It is also possible to operate the pump section with the reverse conveying direction, with the blood being sucked in along the motor housing 20 and exiting from the opening 37.

The motor shaft 25 is mounted in radial bearings 27 and 31 at the proximal end of the motor housing, on the one hand, and at the distal end of the motor housing, on the other hand. Furthermore, the motor shaft 25 is also mounted axially in an axial bearing 39. Should the blood pump be used for conveying blood also or only in the reverse direction, a corresponding axial bearing 39 is also/only provided at the proximal end of the motor housing 20 in a corresponding manner.

It is stressed that the blood pump described above is just an example, the present invention also being applicable to different blood pumps comprising an electric motor, i.e. requiring permanent magnets.

Intravascular blood pumps must meet numerous requirements. Due to their placement within a living body they should be as small as possible. The smallest pumps presently in use have an outer diameter of about 4 mm. Nevertheless, the pumps must convey high-volume flows in human blood circulation. Therefore, the minute pumps have to be high-performance engines.

Furthermore, the implantable blood pumps must not detrimentally influence their biological environment such as the blood to be pumped and the surrounding tissue. Therefore, the pumps should be biocompatible in a broad sense, i.e. they should not contain or produce any potentially noxious materials or considerable heat that might damage the body or constituents thereof.

In addition, replacement of a pump is burdensome to the patient. It follows from this, and of course also from financial considerations, that intravascular blood pumps should have a long useful life.

Materials and design of the intravascular blood pumps must be appropriately selected and specifically adapted to meet these various requirements.

Importantly, an appropriate permanent magnet for the electric motor must be selected. With regard to efficiency and longevity of the pump, the magnet should have a strong magnetic field, i.e. high remanence, high resistance to demagnetization, i.e. high coercivity, and a high saturation magnetization. In this respect, rare-earth permanent magnets, in particular those having neodymium as the rare-earth metal, and especially neodymium iron boron (NdFeB) permanent magnets, are the magnets of choice. Other rare-earth iron boron permanent magnets may also be used.

The stronger the magnet, the smaller the magnet can be while still generating sufficient rotational force. Thus, the stronger the magnet, the smaller the electric motor can be. NdFeB permanent magnets are the strongest permanent magnets currently available. They seem to be ideal for use in intravascular blood pumps.

It is well-known that the magnetic properties of rare-earth metal based magnets, for example of NdFeB magnets, depend on the particular alloy composition, microstructure, and the manufacturing techniques employed. NdFeB magnets are available as polymer-bonded magnets and as sintered magnets. Sintered magnets are superior in magnetic properties. They are prepared by alloying the raw materials, grinding to powder, pressing and sintering. During or after preparation, an external magnetic field is applied in order to magnetize the material. A well-studied magnet is a fine-crystalline sintered material wherein Nd2Fe14B crystals are surrounded by a thin layer particularly rich in neodymium.

While neodymium iron boron magnets have magnetic properties rendering them particularly suitable for use in electric motors of intravascular blood pumps, they also have a serious disadvantage. Namely, commercially available NdFeB magnets, which consist mainly of neodymium, iron and boron, and in particular the sintered neodymium iron boron magnets which have a very active neodymium-rich phase at the grain boundaries, are very vulnerable to corrosion. The magnets may be, for example, corroded by oxygen and moisture in air, in particular, but not only, at the grain boundaries. The corrosion leads to a profound decrease in the magnetic properties, and if the corrosion progresses while the magnet is in use, the performance of the blood pump using the magnet deteriorates. The phenomenon is exacerbated by the tendency of neodymium iron boron magnets to act as a sponge for corrosion products, breaking the structure and leading to spalling off of pieces from the surface of the magnet and finally to crumbling of the magnet.

Unfortunately, liability to corrosion is a property which is common to all rare-earth metals. Therefore, all rare earth metal-based permanent magnets have an unfavorable tendency to corrode, as explained for NdFeB magnets above. For currently available magnets it can be said, as a rule of thumb, that the stronger the magnet, the greater its liability to corrosion.

In an intravascular blood pump, the magnets have to work in a corrosive environment, namely, in the purging liquid flowing between the rotor and the stator (see FIG. 1). As described above, the purge fluid is typically an aqueous fluid, possibly a fluid containing chloride. Chloride is highly corrosive for rare earth metal-based magnets, but also water, and oxygen dissolved in the water, cause severe corrosion within very short time spans of only a few hours.

Clearly, rare earth metal-based permanent magnets, such as neodymium iron boron magnets, for intravascular blood pumps need to be protected against corrosion.

Various measures for protecting neodymium iron boron magnets and other rare earth metal-based magnets against corrosion are known. For example, corrosion resistance may be improved by coating the magnets with protective coatings.

Usual coatings are nickel coatings and coatings based on epoxy resins, and, especially for blood pumps, titanium coatings and Parylene coatings are known. These coatings, however, also have disadvantages. Even if biocompatible metals and organic resins are respectively selected, such as titanium and Parylene, there is the problem that metal coatings must be relatively thick in order to provide sufficient protection. As a result, the gap between the magnet and the windings in the electric motor of the blood pump must be relatively large. A large gap has a strong negative effect on the performance of the electric motor. A large gap demands a higher motor current, and high motor currents produce undesirable heat which may lead to damage of blood and tissue.

Further, organic materials such as Parylene have thermal expansion coefficients which are considerably different from the thermal expansion coefficient of the magnet. Therefore, temperature variations during use of the magnet often lead to cracking and/or delamination of the coating.

EP 3 319 098 A1 discloses a coating for permanent magnets comprising a metal layer, a metal-oxide layer having a thickness of a few nanometers such as e.g. naturally formed upon exposure of an aluminum layer to air, a linker layer, and a layer of poly(2-chloro-p-xylylene). The coating provides good corrosion protection. However, the production process lacks high reproducibility, but rather yields an undesirably high number of magnets being insufficiently protected against corrosion, in particular when coatings are made thin. Further improvement is desirable.

At present, no biocompatible coating for permanent magnets, e.g. neodymium iron boron magnets, is known to fulfil all the requirements for use in an intravascular blood pump in a satisfactory manner. Such a coating must be excellent in corrosion resistance itself, must be thin but nevertheless dense, must not develop cracks or other defects during use, and must reliably and closely adhere to the magnet. Furthermore, the coating process should yield highly reproducible results, i.e. the number of magnets that must be sorted out, should be low. Of course, the coating must be biocompatible, and it must coat with uniform thickness either the complete magnet or at least those portions of the magnet which are exposed to a corrosive environment during use of the magnet. This is particularly demanding because many magnets have a porous surface and a shape comprising edges. Therefore, permanent magnets such as rare earth metal-based magnets, e.g. neodymium iron boron magnets, for use in intravascular blood pumps constitute items which cannot be easily coated with a uniform thickness.

The present invention provides a solution to the problems described above.

The present invention provides permanent magnets having a protective coating thereon which reliably protects the magnets against corrosion while in use in an intravascular blood pump over an extended period of time, and a method for producing the protective coating with high reproducibility. The protective coating is particularly thin, thus allowing to produce very small magnets and, therefore, very small blood pumps.

The subject-matter of the present invention involves a corrosion-resistant permanent magnet, a method for producing a corrosion-resistant permanent magnet, and an intravascular blood pump. Embodiments of the invention are recited below:

1. A corrosion-resistant permanent magnet comprising
 a magnet body, and
 a composite coating provided on and covering surfaces of the magnet body, the composite coating comprising a first layer structure on the magnet body, and optionally a second layer structure on the first layer structure, each layer structure comprising, in the order recited, an inorganic layer,
 a linker layer on the inorganic layer,
 an organic layer formed from poly(2-chloro-p-xylylene) on the linker layer,
 wherein
 the inorganic layer of the first layer structure either comprises an aluminum layer on the magnet body, or comprises an aluminum layer on the magnet body and an aluminum oxide layer on the aluminum layer, and
 the inorganic layer of the second layer structure comprises at least one of an aluminum layer and an aluminum oxide layer, and
 the composite coating has at least one aluminum oxide layer having a thickness of at least 50 nm.

2. The magnet of embodiment 1, wherein a linker layer is provided between the first layer structure and the second layer structure.

3. The magnet of embodiment 1 or 2, wherein the inorganic layer of the second layer structure is an aluminum oxide layer.

4. The magnet of any one of embodiments 1 to 3, wherein the magnet body is a sintered magnet body.

5. The magnet of any one of embodiments 1 to 4, wherein the magnet body is rare earth metal-based.

6. The magnet of embodiment 5, wherein the rare-earth metal is neodymium.

7. The magnet of any one of embodiments 1 to 6, wherein the magnet body is a rare-earth metal iron boron permanent magnet.

8. The magnet of embodiment 6 or 7, wherein the magnet body is a sintered magnet body having Nd2Fe14B crystals and a neodymium iron boron material surrounding the Nd2Fe14B crystals, said neodymium iron boron material being richer in neodymium than the Nd2Fe14B crystals.

9 The magnet of any one of embodiments 1 to 8, wherein the magnet body is rod-shaped with all edges being rounded.

10. The magnet of any one of embodiments 1 to 9, wherein the linker forming at least one of the linker layers is selected from silanes, and silanes having a thiol, phosphine or disulfide group.

11. The magnet of embodiment 10, wherein the silanes are selected from trimethoxy- and triethoxysilanes having an acryloyloxy or methacryloyloxy functional group, or linkers having bis-trimethoxysilyl functional groups.

12. The magnet of embodiment 10, wherein the silanes have a hydride functional group.

13. The magnet of embodiment 10, wherein the linker is selected from 3-(2-pyridylethyl)thiopropyl trimethoxysilane, 3-(4-pyridylethyl)thiopropyl trimethoxysilane, and 2-(diphenylphosphino)ethyl triethoxysilane.

14. The magnet of any one of embodiments 1 to 13, wherein the thickness of the aluminum layer of the first layer structure and/or the second layer structure is from 0.5 μm to 15 μm.

15. The magnet of embodiment 14, wherein the thickness of the aluminum layer of the first layer structure and/or the second layer structure is from 1 μm to 10 μm, or from 1 μm to 5 μm.

16. The magnet of any one of embodiments 1 to 15, wherein the thickness of the aluminum oxide layer of the first layer structure and/or the second layer structure is from 50 nm to 200 nm.

17. The magnet of embodiment 16, wherein the thickness of the aluminum oxide layer of the first layer structure and/or the second layer structure is from 80 nm to 120 nm.

18. The magnet of any one of embodiments 1 to 17, wherein the first layer structure and/or the second layer structure has an inorganic layer comprising an aluminum layer and an aluminum oxide layer, and wherein the combined thickness of the aluminum layer and the aluminum oxide layer of the first layer structure and/or the second layer structure is in a range from 5 μm to 15 μm.

19. The magnet of any one of embodiments 1 to 18, wherein at least one of the linker layers is a monolayer, or wherein at least one of the linker layers has a thickness of from 20 nm to 50 nm.

20. The magnet of any one of embodiments 1 to 19, wherein the thickness of the layer formed from poly(2-chloro-p-xylylene) of the first layer structure and/or the second layer structure is in a range from 5 μm to 20 μm.

21. The magnet of any one of embodiments 1 to 20, wherein the thickness of the composite coating is no more than 200 μm, or no more than 50 μm.

22. The magnet of any one of embodiments 1 to 21, wherein all layers of the composite coating completely extend over all surfaces of the magnet body.

23. A method for producing a corrosion-resistant permanent magnet, the method comprising
 providing a non-magnetized magnet body,
 forming a first layer structure on the magnet body by depositing an inorganic layer on surfaces of the magnet body, depositing a linker layer on the inorganic layer, and depositing a layer of poly(2-chloro-p-xylylene) on the linker layer, and optionally
 forming a second layer structure on the first layer structure by depositing an inorganic layer on the first layer structure, depositing a linker layer on the inorganic layer, and depositing a layer of poly(2-chloro-p-xylylene) on the linker layer, and
 magnetizing the magnet body,
 wherein
 depositing the inorganic layer of the first layer structure either comprises depositing an aluminum layer on the magnet body, or comprises depositing an aluminum layer on the magnet body and an aluminum oxide layer on the aluminum layer,
 depositing the inorganic layer of the second layer structure comprises depositing an aluminum layer on the first layer structure, or comprises depositing an aluminum oxide layer on the first layer structure, or comprises depositing an aluminum layer on the first layer structure and an aluminum oxide layer on the aluminum layer, at least one aluminum layer is deposited by a physical vapor deposition process, and at least one aluminum oxide layer is deposited by an atomic layer deposition process to a thickness of at least 50 nm.

24. The method of embodiment 23, wherein a linker layer is deposited on the first layer structure.

25. The method of embodiment 23 or 24, wherein an aluminum oxide layer is deposited as the inorganic layer of the second layer structure.

26. The method of any one of embodiments 23 to 25, wherein the magnet body is a magnet body as defined in any one of embodiments 4 to 9.

27. The method of any one of embodiments 23 to 26, wherein two aluminum layers are formed, one of the aluminum layers being formed by ion vapor deposition or plasma deposition or atomic layer deposition.

28. The method of any one of embodiments 23 to 27, wherein the aluminum oxide layer of the first layer structure and/or the second layer structure is formed from AlX3 as a first precursor compound and H2O as a second precursor compound, with X representing lower alkyl groups, which may be the same or different, or representing a hydrogen atom and lower alkyl groups, which may be the same or different, or representing halogen atoms, which may be the same or different.

29. The method of embodiment 28, wherein AlX3 is selected from the group consisting of trimethyl aluminum (TMA), triethyl aluminum (TEA), triisobutyl aluminum (TIBA), dimethyl aluminum (DMAIH) and AlCl3.

30. The method of any one of embodiments 23 to 29, wherein at least one of the linker layers is formed by applying a linker by physical vapor deposition using plasma, or by physical vapor deposition without using plasma, or by depositing a linker from a solution.

31. The method of any one of embodiments 23 to 30, wherein the linker of at least one of the linker layers is a linker as defined in any one of embodiments 10 to 13.

32. The method of any one of embodiments 23 to 31, wherein the layer of poly(2-chloro-p-xylylene) of the first layer structure and/or the second layer structure is formed by plasma deposition of dichloro[2.2]paracyclophane.

33. The method of any one of embodiments 23 to 32, wherein the layers of the first layer structure and/or the second layer structure have thicknesses as defined in any one of embodiments 14 to 21.

34. An intravascular blood pump comprising an electric motor, wherein the electric motor comprises a permanent magnet as defined in any one of embodiments 1 to 22.

A magnet is corrosion resistant in the sense of this invention if it passes the test described in the experimental section.

According to the present invention, a strong permanent magnet comprises a coating either completely surrounding a magnet body or covering at least those surfaces of the magnet body which are exposed to fluid when the magnet is operating in an intravascular blood pump. The coating renders the magnet resistant to corrosion while in use in an intravascular blood pump. Preferred magnet bodies are sintered magnets consisting primarily of neodymium, iron, and boron, with fine tetragonal magnetic Nd2Fe14B crystals and a neodymium rich non-magnetic phase surrounding the crystals, as described above. Typically, the Nd2Fe14B crystals forming the main phase have a mean crystal diameter within a range of 1 to 80 μm. The non-magnetic neodymium rich phase makes up from 1% to 50% by volume of the magnet body. These magnets are readily available commercially. They are preferred because they have high magnetic characteristics, and because they are particularly strong, i.e. have a high flux density. For the reasons indicated above, an application in intravascular blood pumps requires particularly strong magnets. In principle, however, the inventive corrosion-resistant coating can be applied to any material requiring protection against corrosion, for example different rare-earth iron boron magnetic materials or any other magnetic materials.

The inventive coating is a composite coating provided on surfaces of the magnet body, i.e. the actual magnetic material. The composite coating comprises a layer structure which comprises, in the order recited, an inorganic layer, a linker layer on the inorganic layer, and an organic layer formed from poly(2-chloro-p-xylylene) on the linker layer. The inorganic layer is provided on surfaces of the magnet body. The inorganic layer comprises either an aluminum layer, or a combination of an aluminum layer and an aluminum oxide layer. In any case, the aluminum layer is the layer provided on surfaces of the magnet body.

The layer structure comprising the aluminum layer on surfaces of the magnet body, optionally the aluminum oxide layer on the aluminum layer, the linker layer on the aluminum layer or the aluminum oxide layer, and the organic layer on the linker layer may constitute the composite coating or may constitute only a first part thereof. Namely, a further (second) layer structure may be provided on the first layer structure and cover surfaces of the organic layer of the first layer structure. The second layer structure is similar to the first layer structure, but does not need to be identical to the first layer structure.

The second layer structure comprises, in the order recited, an inorganic layer on the organic layer of the first layer structure, a linker layer on the inorganic layer, and an organic layer formed from poly(2-chloro-p-xylylene) on the linker layer. The inorganic layer of the second layer structure comprises an aluminum layer, or an aluminum oxide layer, or a combination of an aluminum layer and an aluminum oxide layer. Either the aluminum layer or the aluminum oxide layer may be provided on the organic layer of the first layer structure.

A further linker layer may be provided between the first layer structure and the second layer structure in order to enhance bonding between the organic layer of the first layer structure and the inorganic layer of the second layer structure.

In a composite coating comprising a first layer structure and a second layer structure, the same or different compounds may be used for the linker layers, and corresponding layers of the first layer structure and the second layer structure may have the same thickness or different thicknesses. However, the composite coating comprises at least one aluminum oxide layer having a thickness of at least 50 nm. In composite coatings having a first layer structure and a second layer structure, the aluminum oxide layer having a thickness of at least 50 nm may be a constituent of the first layer structure or of the second layer structure. Alternatively, both layer structures may comprise an aluminum oxide layer having a thickness of at least 50 nm.

In the following, the constituents of the first layer structure or of a single-layer structure will be designated a first inorganic layer (first aluminum layer, first aluminum oxide layer), a first linker layer, and a first organic layer, even if there is only one single-layer structure provided on the magnet body. Analogously, the constituents of the second layer structure are designated a second inorganic layer (second aluminum layer, second aluminum oxide layer), a second linker layer, and a second organic layer. A linker layer, if present between the first layer structure and the second layer structure, will be designated a further linker layer.

Rare earth metal-based magnets as purchased from a supplier are typically protected by a phosphate coating. This phosphate coating may be removed, for example by washing with an acid, prior to application of the composite coating. However, the phosphate coating does not detrimentally interfere with the coating or the coating process according to the present invention and may, therefore, remain on the magnet body. Preferably, the phosphate coating is not removed. Not removing the phosphate coating saves one process step and avoids introducing impurities during such a process step. It is, however, preferable to clean the magnet prior to application of the aluminum layer of the first layer structure (or the only layer structure, respectively). Cleaning is preferably performed by washing the magnet with an organic solvent, for example an alcohol. Particularly preferred cleaning agents are isopropanol and a mixture of isopropanol and ethanol. After washing with an organic solvent, the magnet is dried, for example in vacuum or in an air stream.

After cleaning and drying, the aluminum layer is applied to the surface of the magnet body.

Methods for applying the aluminum layer are in principle not particularly limited. Exemplary application methods include dry methods and wet methods.

An exemplary wet method is galvanic deposition (electroplating), for example out of ionic liquids in a manner as usual in the art. Electroplating is a very common application method for aluminum coatings, and is regarded as an easily controllable, low-cost method yielding good-quality coatings in a well reproducible manner. However, galvanic deposition has been proved less advantageous for the purpose of the present invention. The present invention requires coatings of a particularly high quality, and it appears that galvanic deposition cannot produce aluminum coatings having the desired quality with the desired reproducibility.

Exemplary dry methods are physical vapor deposition (PVD) and ion vapor deposition (IVD), and methods such as plasma coating and atomic layer deposition (ALD). IVD yields aluminum layers having column like structures. Peening is advisable before depositing further layers thereon. Such aluminum layers also do not have the desired quality. PVD, and in particular Arc-PVD, is the preferred method for producing the aluminum layer of the composite coating of the present invention. PVD can produce aluminum layers having the desired quality and thickness within a reasonable time and at a reasonable cost. In particular, PVD produces homogeneous aluminum layers. Therefore, the composite coating of this invention comprises at least one aluminum layer which has been deposited by PVD, preferably Arc-PVD. In composite coatings comprising more than one aluminum layer, the additional aluminum layer can be deposited by a different process, for example IVD, however, preferably both aluminum layers are deposited by PVD, in order to benefit from the advantages of homogeneous aluminum barriers at different locations within the composite coating.

Exemplary reaction conditions for the PVD process of applying a first aluminum layer or a second aluminum layer are a temperature in the range from about 200° C. to 260° C., and an inert gas atmosphere, for example an argon gas atmosphere.

ALD is equally applicable, however, is time consuming and expensive.

Exemplary aluminum layers have a thickness from 0.5 μm to 15 μm. From the viewpoint of providing optimum corrosion protection, the aluminum layer or aluminum layers, respectively, are desirably thick, however, the thicker the layer, the more time is required for its application (rendering the process expensive) and, as described above, thick coatings are disadvantageous in that they increase the distance between the magnet body and the windings in the electric motor of the blood pump. Therefore, a preferred thickness is 15 μm or below. On the other hand, sufficient corrosion protection cannot be reliably provided by composite coatings comprising an aluminum layer having a thickness below 0.5 μm. This applies also to coatings having more than one aluminum layer. Therefore, a preferred thickness is 0.5 μm or above. A more preferred thickness of the aluminum layer is from 1 μm to 10 μm, and a particularly preferred thickness is from 1 μm to 5 μm, irrespective of whether the aluminum layer is in the first layer structure or in the second layer structure.

Aluminum forms a passivating oxide layer when exposed to air. This naturally formed (native) oxide layer is only a few nanometers thin, typically only about 2 of 3 nm, and adheres well to the underlying aluminum metal layer. It has been found that corrosion protection of composite coatings comprising an aluminum layer can be improved when the aluminum oxide layer thickness is increased considerably beyond the thickness of native aluminum oxide layers. A preferred thickness range is from 50 to 200 nm. It is advantageous, but not indispensable, that the aluminum oxide layer is formed on an underlying aluminum layer. Rather, an aluminum oxide layer may be also formed on an organic layer such as a poly(2-chloro-p-xylylene) layer of an underlying first layer structure, or on a linker layer on the first layer structure.

In the present invention, the aluminum oxide layer is preferably applied by atomic layer deposition (ALD). In principle, other deposition processes are also possible, such as anodic oxidation, which can produce aluminum oxide layers having a thickness of up to 1 μm at low cost. However, composite coatings comprising aluminum oxide produced by anodic oxidation are inferior as regards endurance of corrosion protection. It is believed that the reason is the microscopic structure of the aluminum oxide layers. Anodic oxidation forms layers having minute channels extending through the layers and comprising ions therein. These channels must be plugged by overlying layers, and if some channels remain open, or if some channels get exposed during use of a coated magnet, due to wear or corrosion of the overlying layers, the respective channels provide an entry for the corrosive purge fluid. Making the coating thick, for example from 500 to 1.000 nm, can somewhat compensate this disadvantage.

Methods yielding aluminum oxide layers free of channels, for example PVD and IVD, are more preferable, and allows reducing the aluminum oxide layer thickness for example to a range from about 200 to 500 nm, while still providing for sufficient corrosion protection.

However, the method of choice for forming the aluminum oxide layer is atomic layer deposition (ALD). Therefore, the composite coating of this invention comprises at least one aluminum oxide layer which has been deposited by atomic layer deposition. This aluminum oxide layer has a thickness of at least 50 nm, and it may constitute a layer of the first layer structure or of the second layer structure. Irrespective of whether the aluminum oxide layer is a constituent of the first layer structure or the second layer structure, it is deposited by an ALD process to a layer thickness of at least 50 nm, preferably 50 nm to 200 nm, and more preferably from 80 nm to 120 nm. In a composite coating comprising a first layer structure and a second layer structure, only one of the layer structures must have an aluminum oxide layer deposited by ALD to a thickness of at least 50 nm. The other layer structure may or may not comprise an aluminum oxide layer, and if it comprises an aluminum oxide layer, this layer may be deposited by ALD or by a different process.

ALD is a thin-film deposition method in which a film is grown on a substrate by exposing the substrate surface to alternate gaseous substances, so-called precursors. The precursors are introduced into a reactor containing the substrate to be coated in a series of sequential, non-overlapping pulses, i.e. the precursors are never present simultaneously in the reactor.

In each pulse, the precursor which has been introduced into the reactor is adsorbed on the surface of the substrate to be coated until all available reactive sites on the surface are consumed. Then, any excess precursor is removed from the reactor. Thereafter, a second precursor, different from the first precursor, is introduced into the reactor and adsorbed on the substrate surface, undergoing a chemical reaction with the previously adsorbed first precursor. Then again, any excess precursor and gaseous reaction products are removed from the reactor. Depending on the type of layer to be deposited, further precursors, different from the first and second precursors, may be introduced into the reactor, adsorbed and reacted, and any excess precursors and reaction products removed from the reactor.

A single exposure to all of the precursors is called an ALD cycle.

Ideally, each ALD cycle produces a monolayer of coating material. Therefore, ALD allows controlling layer thickness and composition at an atomic level. It can coat large substrates having complex shapes with uniform and conformal coatings without defects which might constitute a site rendering the composite coating more susceptible to attacks by corrosive agents.

In the present invention, the artificially created aluminum oxide layer may be formed on an aluminum layer or on a native oxide layer already formed on the aluminum layer, on the organic layer of the first layer structure or on a linker layer between the first and the second layer structure. Preferred precursor materials for performing the ALD process are AlX3 and water (in gaseous form). In AlX3, X represents lower alkyl groups (which may be the same or different), or lower alkyl groups (which may be the same or different) and hydrogen, or halogen atoms (which may be the same or different). Particularly preferred AlX3 compounds are trimethyl aluminum (TMA), triethyl aluminum (TEA), triisobutyl aluminum (TIBA), dimethyl aluminum (DMAIH), and aluminum trichloride (AlCl3).

In an exemplary ALD process for producing the aluminum oxide layer of a first layer structure or a second layer structure or both, the magnet is placed in a reaction chamber, and AlX3 in a suitable inert carrier gas, for example argon, and at an appropriate temperature, for example about 300° C., is introduced into the reaction chamber. The AlX3 adsorbs on the surface (aluminum or naturally formed aluminum oxide or organic layer or linker layer) almost instantaneously, and any excess AlX3 and carrier gas is removed by evacuating, for example to about 0.1 to 0.01 Pa.

Thereafter, humid air is introduced. The water contained therein adsorbs on the surface and reacts with AlX3, forming aluminum oxide on the surface as well as HX. The air and any excess AlX3 as well as HX is removed by evacuating the reaction chamber again to about 0.1 to 0.01 Pa.

The complete ALD cycle takes from about 10 to 12 seconds and produces an aluminum oxide coating layer thickness of about 0.1 nm. Thus, producing a particularly preferred aluminum oxide layer thickness of about 100 nm requires an ALD process time of about 3 hours.

The thickness of a combined aluminum/aluminum oxide layer is preferably small, i.e. about 15 μm or less. A thickness of 10 μm or less is particularly preferred.

In order to enhance the corrosion protection provided by the inorganic layer, the inorganic layer is combined with a poly(p-xylylene) polymer layer. Poly(p-xylylene) polymers are known under the trade name Parylene. Parylenes may react with hydroxyl group-containing surfaces, and are known to form pin hole-free coatings at low layer thicknesses. In addition, they have low dielectric constants (about 3), which is advantageous in implantable blood pumps. A composite coating comprising aluminum and/or aluminum oxide layers and a Parylene layer is biocompatible and also provides corrosion protection. However, the adhesion of the Parylene layer to the aluminum or the aluminum oxide layer is not sufficiently strong under the working conditions in an intravascular blood pump. The Parylene layer starts to delaminate after an unacceptably short time, thus exposing the aluminum or the aluminum oxide layer. The inorganic layer cannot sufficiently protect the magnet body, and thus corrosion of the magnet body sets in.

According to the present invention, this scenario is prevented by a combination of several measures: provision of an interface layer linking the inorganic layer and the Parylene layer, use of a particular Parylene compound, provision of at least one aluminum layer having a homogeneous structure such as obtainable by physical vapor deposition, and provision of at least one comparatively thick aluminum oxide layer having a dense and nearly defect-free structure, such as obtainable by ALD deposition.

The compound forming the interface layer in the first and/or second layer structure, or between the first layer structure and the second layer structure, i.e. the linker compound, must be bifunctional. Bifunctional means that the linker compound must have two types of functional groups or molecular moieties of different functionality (reactivity), one functional group or molecular moiety bonding to the inorganic layer, e.g. by reacting with surface hydroxyl groups of the inorganic layer, and the other functional group or molecular moiety bonding to Parylene, thus firmly linking the inorganic layer and the organic Parylene layer. Linking may be provided by covalent bonds or other bonds, e.g. by van der Waals forces.

Linkers having functional groups or moieties bonding to metals or metal oxides, and functional groups or moieties bonding to Parylene, are known. As exemplary linkers, mention may be made of silane compounds, mercaptans, phosphines, disulfides, and silanes having a thiol, phosphine or disulfide group.

In the present invention, linkers are preferably alkoxysilanes, such as methoxysilanes and ethoxysilanes, for example silanes having the formula (H3CO)3Si—R, with R being e.g. methacrylate, alkylamine, phenylamine, or epoxyalkyl. For bonding to Parylene, the linkers preferably have an acryloyloxy or methacryloyloxy functional group. The carbon chain length between the silyl portion and the (meth)acryloyloxy portion of the linker typically has from 1 to 16 carbon atoms (methyl, ethyl, propyl, butyl, pentyl . . . ). The hydrocarbon chain is typically saturated, but may also contain one or more unsaturated bonds. A particularly preferred linker is 3-(trimethoxysilyl) propyl methacrylate (A-174) from Silquest, but other silane compounds such as G-170 from Silquest (a vinyl-functional silane coupling agent) are also suitable. In addition, linkers having bis-trimethoxysilyl or bis-triethoxysilyl functionalities may be used, for example bis(trimethoxysilylethyl)benzene.

The bifunctional linkers are preferably applied to the surface (aluminum or aluminum oxide of the first or second layer structure, or Parylene layer of the first layer structure) by a plasma coating process or by physical vapor deposition without plasma or by applying an aprotic, or an alcoholic or an aqueous solution of the bifunctional linker compound to the surface to be coated. Dry coating of silane compounds in a plasma chamber yields glassy layers comprising Si—O—Si—O-chains arranged substantially parallel to the inorganic surface and bonded to the surface via oxygen atoms. An organic residue faces away from the surface and is available for bonding to the Parylene. Physical vapor deposition and wet application form interface layers having a similar structure, but without a glassy appearance.

Plasma deposition yields a dense layer with acceptable adherence to Parylene. Physical vapor deposition without plasma yields less dense layers having better adherence to Parylenes than plasma deposited layers. Wet application yields very dense monolayers having an irregular network and a high degree of crosslinking and a high percentage of silicon-bonded oxygen. These layers also adhere very well to Parylene layers. Therefore, wet application is particularly preferable.

Alternatively, plasma application and physical vapor deposition (without plasma) or wet application processes can be combined, i.e. a glassy interface layer is first formed by plasma deposition, followed by physical vapor deposition or wet application of a second linker layer, thus forming a composite linker layer. In such composite linker layer, silicon atoms of the glassy layer are linked covalently to oxygen atoms of the second layer, with organic residues (such as methacrylate, alkylamine, or epoxyalkyl) of the second layer being available for bonding the Parylenes, either covalently or in a different manner, e.g. by van der Waals forces.

The interface layer typically has a thickness in the range from 10 to 100 nm, preferably from 20 to 50 nm. Alternatively, only a monolayer may be applied. Monolayers are obtainable via application of a solution of the linker compound, and evaporation of the solvent.

In the first layer structure and, if present, in the second layer structure, a Parylene layer, i.e. a poly(p-xylylene) polymer layer, is formed on the interface layer. Poly(p-xylylene) polymers have the structural formula

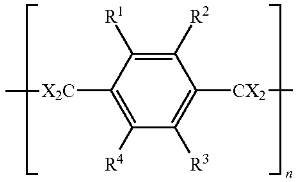

wherein n is the polymerization degree.

Precursors of poly(p-xylylene) compounds are [2.2]paracyclophanes having the structural formula

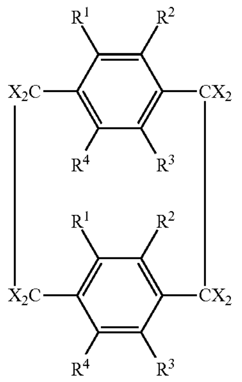

The dimeric compounds are available on the market, for example precursors of Parylene N, Parylene C, Parylene D, and Parylene F. In Parylene N, all of X and R1 to R4 are hydrogen, in Parylene C, one of R1 to R4 is chlorine while the other residues R as well as X are hydrogen, in Parylene D, two of the residues R1 to R4 are chlorine while all other residues are hydrogen, and in Parylene F, the residues X are fluorine while the residues R1 to R4 are hydrogen. Parylene layers are typically used as moisture barriers and dielectric barriers.

At high temperatures (above about 500° C., depending on the particular Parylene) under vacuum, the dimers are cracked to form the corresponding p-xylylene radicals. The monomers polymerize to form poly(p-xylylene) polymers, on the one hand, and bond to the interface layer via the functional groups thereof, e.g. methacrylate groups, on the other hand. Alternatively, they may simply adhere to hydrophobic portions of the interface layer.

According to this invention, it has been found that Parylene C, wherein one of R1 to R4 is chlorine, forms a coating rendering magnetic materials resistant to corrosion under the conditions encountered in intravascular blood pumps, when applied as the cover layer of the first layer structure, and of the optional second layer structure, of the composite coating of the invention. The Parylene C layer is preferably applied by plasma deposition, and the layer thickness is preferably in a range from 5 to 25 μm, more preferably from 10 to 20 μm. A thickness of about 15 μm is particularly preferred.

When Parylene C is applied directly onto the surface of the magnetic material, crack formation and delamination of the protective Parylene C layer and corrosion of the magnetic material are observed within a few days. Likewise, if Parylene C is applied onto an aluminum layer or an aluminum/aluminum oxide layer, corrosion of the magnetic material is observed under the conditions in an intravascular blood pump within an unacceptably short time period, due to delamination. In addition, Parylene compounds different from Parylene C do not provide sufficient corrosion protection, even if an adhesion promoter is used, e.g. if applied on a silane-based interface layer.

The composite coating of the present invention adheres well to the magnet body, and since it has a structure made up of both inorganic and organic constituents, it provides an effective barrier against both inorganic and organic matter. The barrier properties are further enhanced by the particularly homogeneous structure of the aluminum layer deposited by PVD, and the particularly dense structure of the aluminum oxide layer deposited by ALD. In addition, glassy interface layers have barrier properties, too.

In an embodiment of the present invention, corrosion protection of the magnetic material is further enhanced by the shape of the magnet body being particularly adapted to allow the formation of a coating covering the magnet body with a uniform thickness. To this aim, the magnet body has no sharp edges, but rather rounded forms such as soft edges. Preferably, the magnet body is rod-shaped having a channel extending therethrough in a longitudinal direction for receiving the motor shaft of an intravascular blood pump, the opposing front faces of the magnet body being beveled towards the channel. The channel does not need to be coated with the composite coating because in an intravascular blood pump the channel receives the motor shaft and is fixed thereto. Of course, the channel may be coated nevertheless, to be on the safe side.

The magnet body may be a single piece, or may be composed of several segments. In the latter case, each segment is provided with the inventive coating either surrounding it completely or at least the exposed surfaces thereof with a uniform thickness. Preferably, each segment has soft edges.

BRIEF DESCRIPTION OF THE DRAWINGS

The present invention will be further explained with reference to the accompanying drawings, wherein.

The drawings are not to scale. They should not be construed as limiting the invention in any manner.

DETAILED DESCRIPTION

Figure 1:
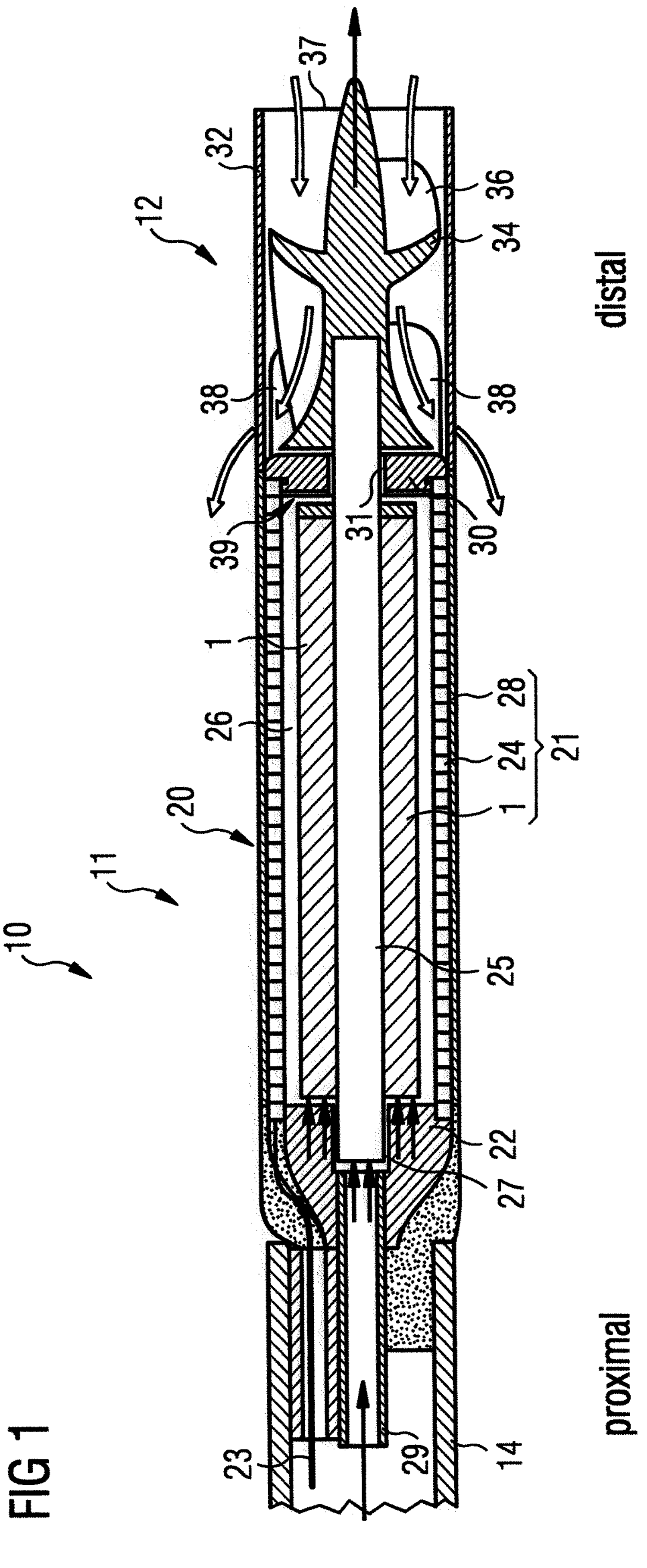
FIG. 1 is a schematic longitudinal section of an exemplary embodiment of an intravascular blood pump.

The intravascular blood pump 10 illustrated in FIG. 1 has been described above. The pump is conventional in construction, but comprises a corrosion-resistant permanent magnet 1 according to the present invention.

In the pump of FIG. 1, the magnet 1 is rod-shaped, the opposing front faces being flat and parallel to each other. While the composite coating according to the present invention may effectively protect a magnet body having sharp edges as illustrated in FIG. 1 against corrosion over an extended period of time, it is preferred in the present invention to use a magnet body having a shape as illustrated in FIG. 4. The individual layers of the composite coating completely extend over each previously applied composite coating layer.

Figure 2:
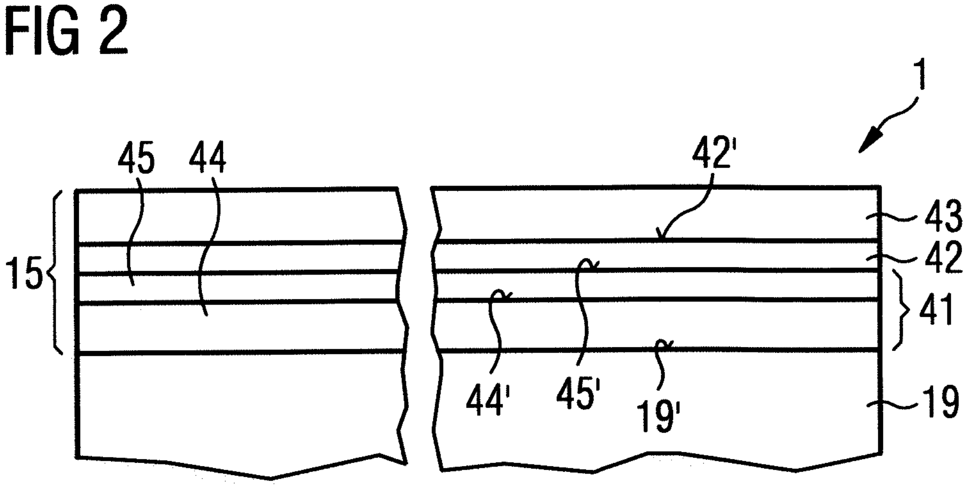
FIG. 2 is a schematic sectional view of a portion of a magnet according to the present invention, the magnet having a composite coating comprising a single-layer structure.

FIG. 2 is a schematic sectional view of a portion of a magnet 1 having a composite coating 15 comprising a single-layer structure (i.e. a “first” layer structure). The composite coating 15 is formed on a surface 19' of a non-magnetized magnet body 19. Composite coating 15 comprises a first aluminum layer 44 formed by physical vapor deposition on surface 19' of magnet body 19. An aluminum oxide layer 45 is deposited by atomic layer deposition on surface 44' of aluminum layer 44. The aluminum layer and the aluminum oxide layer, in combination, constitute the inorganic layer 41 of composite coating 15. A linker layer 42 is formed on surface 45' of the aluminum oxide layer, and firmly bonds the organic layer 43 to the aluminum oxide layer 45. The organic layer 43 of composite coating 15 consists of Parylene C and covers surface 42' of the linker layer 42.

Figure 3:
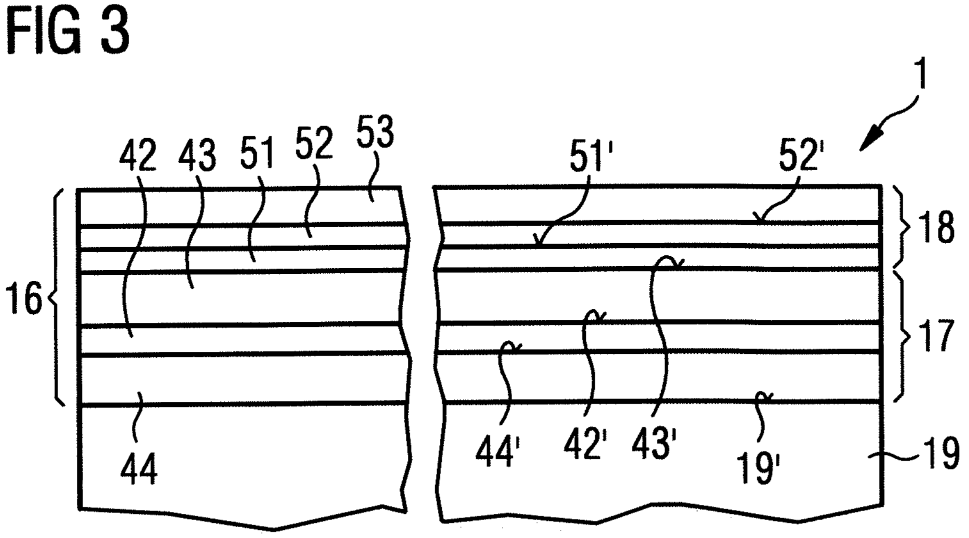
FIG. 3 is a schematic sectional view of a portion of a magnet according to the present invention, the magnet having a composite coating comprising a first layer structure and a second layer structure.

FIG. 3 is a schematic sectional view of a portion of another magnet 1, the magnet having a composite coating 16 comprising a first layer structure 17 and a second layer structure 18.

The first layer structure 17 consists of an aluminum layer 44, a first linker layer 42 and a first organic layer 43. The second layer structure 18 consists of an aluminum oxide layer 51, a second linker layer 52, and a second organic layer 53. The first aluminum layer 44 is formed on surface 19' of a non-magnetized magnet body 19, the first linker layer 42 is formed on surface 44' of the first aluminum layer 44, first organic layer 43 is formed on surface 42' of the first linker layer 42, second aluminum oxide layer 51 is formed on surface 43' of the first organic layer 43, second linker layer 52 is formed on surface 51' of the second aluminum oxide layer 51, and second organic layer 53 is formed on surface 52' of the second linker layer 52. The first and the second organic layers are Parylene C layers. The second organic layer 53 constitutes the outermost layer of composite coating 16.

Although magnet 1 illustrated in FIG. 3 has a composite coating 16 comprising a first layer structure 17 and a second layer structure 18, there is only one aluminum layer (first aluminum layer 44) and only one aluminum oxide layer (second aluminum oxide layer 51). In this respect, composite coating 16 is comparable to composite coating 15 having also only one aluminum layer and only one aluminum oxide layer. Therefore, as in the case of composite coating 15, it is important that aluminum layer 44 is deposited by physical vapor deposition, and aluminum oxide layer 51 is deposited by atomic layer deposition to a thickness of at least 50 nm, in order to obtain optimum layer structures as required for best corrosion resistance.

If an additional aluminum oxide layer is provided between first aluminum layer 44 and first linker layer 42, such aluminum oxide layer does not need to be deposited by ALD, and does not need to have a thickness of at least 50 nm, however, deposition by ALD to a thickness of at least 50 nm is preferred. Similarly, if an additional aluminum layer is provided between first organic layer 43 and second aluminum oxide layer 51, such aluminum layer does not need to be deposited by PVD, but it preferably is.

In the composite coating 16 illustrated in FIG. 3, the second layer structure 18 is formed directly on the first layer structure 17. However, in order to enhance bonding between first layer structure 17 and second layer structure 18, a further linker layer may be applied to surface 43' of the first organic layer 43 prior to application of the second aluminum oxide layer 51, i.e. the second layer structure 18 may be formed on the surface of such further linker layer.

Figure 4A:
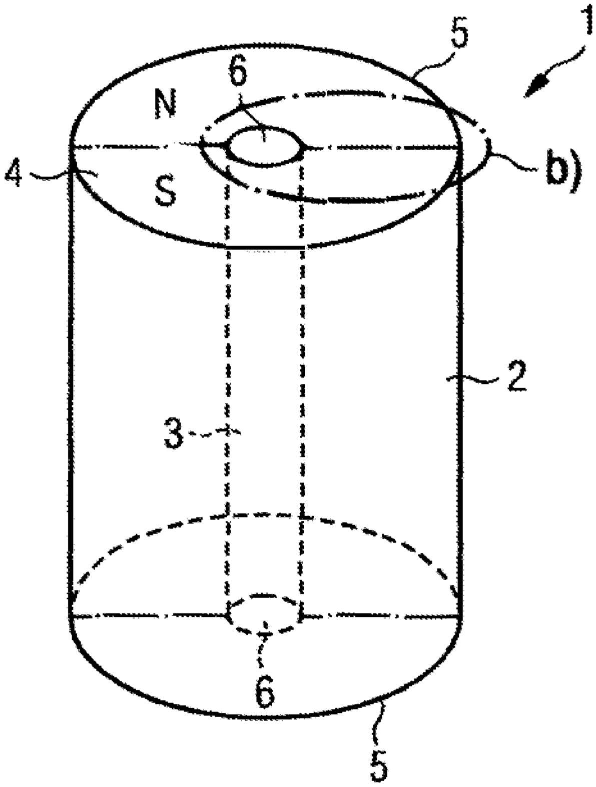
FIG. 4*a* is a schematic representation of an exemplary single-piece magnet according to the present invention.

FIG. 4*a* shows a single-piece magnet 1 having a rod shape and a bore or channel extending therethrough in a longitudinal direction. During use of the magnet in an intravascular blood pump 10 as illustrated in FIG. 1, the channel receives the motor shaft 25. The opposing front faces 4 of the magnet are tapered towards the channel. The magnet 1 has a composite coating according to the invention at the outer surfaces 2 exposed to the fluid flowing in gap 26 and the tapered front faces 4. The inner surfaces 3 adjacent to the motor shaft 25 may or may not be coated. Edge 5 at the transition between the outer surface 2 and the front surface 4, as well as edge 6 at the transition between front surface 4 and the inner surface 3, are coated. The edges are soft, thus facilitating the formation of a well-adhering uniform coating. "N" and "S" indicate the north pole and the south pole of the magnet.

Figure 4B:
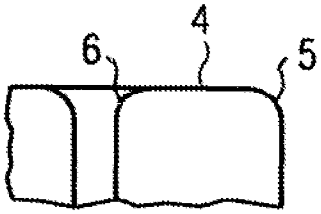
FIG. 4*b* is a partial sectional view showing a detail of the magnet illustrated in FIG. 4*a*.

FIG. 4*b* is a partial sectional view along the dash-dot line in FIG. 4*a*. FIG. 4*b* shows the region of the magnet within the loop in FIG. 4*a*. FIG. 4*b* clearly shows the soft edges 5, 6.

Figure 5:
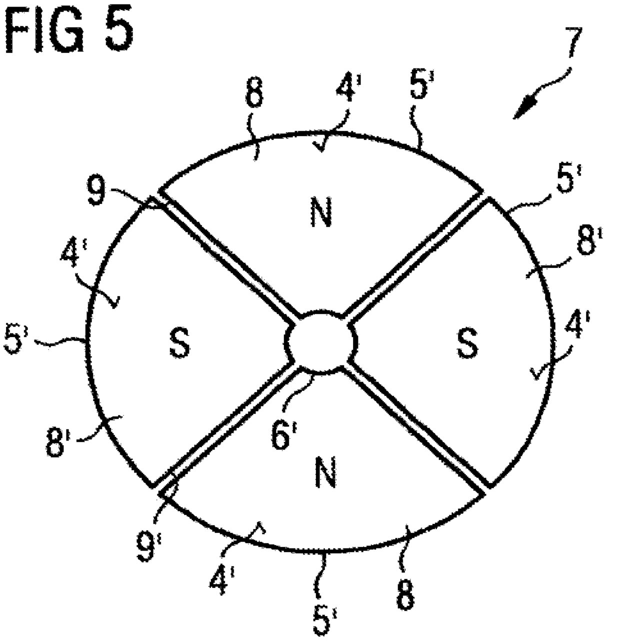
FIG. 5 is a schematic top view of an exemplary segmented magnet according to the present invention.

FIG. 5 shows a segmented magnet 7. The magnet illustrated in FIG. 5 has four segments 8, 8'. Segments 8, which are opposite to one another, have the same magnetic polarity, as indicated by "N" in the top view of FIG. 5, and segments 8', which are also opposite to one another, have the same magnetic polarity, as indicated by "S" in the top view of FIG. 5. As a result, adjacent segments 8, 8' have opposite magnetic polarity.

Segments 8, 8' have, analogously to the single-piece magnet shown in FIG. 4, inner surfaces, outer surfaces, opposing front faces, edges at the transition between the outer surfaces and the front surfaces, and edges at the transition between the front surfaces and the inner surfaces. The front faces are designated 4', and the edges are designated 5' and 6', respectively, in correspondence to the designations in FIG. 4. In addition, segments 8, 8' have side surfaces 9, 9', separated by gaps in the drawing. Of course, when the magnet is in use, side surfaces 9, 9' contact each other. All surfaces of each segment of the magnet may be completely covered by the inventive composite coating, but side surfaces 9, 9' which are not exposed because they contact each other, and the inner surfaces which are not exposed because they contact the motor shaft, do not need to be coated. Preferably all edges of all segments are soft edges.

Table 1 illustrates the results of corrosion testing of niobium iron boron magnets coated with different coatings. Thirteen identical cylindrical non-magnetized $Nd_2Fe_{14}B$ sintered magnet bodies having a length of 12 mm and a diameter of 2.8 mm were coated as described below, and subjected to corrosion testing in an aqueous solution containing 0.9 weight % sodium chloride at 60° C. Test specimens were inspected daily until day 70. The test was stopped after 70 days. Corrosion of the magnetic material results in lifting or deformation of the coating. Thus, lifting of the coating or formation of a bulge at a surface of a test specimen indicates corrosion of the magnetic material. Formation of a bulge having a height of 0.1 mm as well as lifting of the coating were defined as being indicative of magnet failure.

Test specimens were prepared in the following manner:

All specimens: Non-magnetized neodymium iron boron magnet bodies (with phosphate passivation as purchased) were cleaned with isopropanol and then dried in an air stream. Then, coatings were applied, and after application of the coatings, the coated magnets were subjected to magnetization in a magnetic field. Magnetizing the magnet bodies before applying the inventive composite coating is not appropriate. Coating thicknesses were about 1 μm, 2 μm, and 3 μm, respectively, for the aluminum layer, about 60 nm for the aluminum oxide layer of specimen samples 4, 5 and 6, and about 100 nm for all other specimen samples, about 1 monolayer for the silane layer, and about 15 μm (+2 μm) for the Parylene layer, where applicable.

Unless otherwise indicated, aluminum layers were applied by Arc-PVD, aluminum oxide layers were applied by ALD, using TEA as a precursor compound, the silane adhesion promoter (Silane A-174) was applied from an aqueous solution, and Parylene C was also applied by plasma coating. The adhesion promotor constitutes the linker.

Specimens 1 to 3: the dry magnet bodies were provided, in the recited order, with layers consisting of aluminum (layer thickness for specimen 1: 1 μm, for specimen 2: 2 μm, and for specimen 3: 3 μm), aluminum oxide, adhesion promotor, and Parylene C.

Specimens 4 to 6: dry magnet bodies were provided, in the recited order, with layers consisting of aluminum (layer thickness for specimen 4: 1 μm, for specimen 5: 2 μm, and for specimen 6: 3 μm), adhesion promotor, Parylene C, aluminum oxide, adhesion promoter, and Parylene C.

Specimens 7 to 9: dry magnet bodies were provided, in the recited order, with layers consisting of aluminum (layer thickness for specimen 7: 1 μm, for specimen 8: 2 μm, and for specimen 9: 3 μm), adhesion promotor, and Parylene C.

Specimens 10 to 12: dry magnet bodies were provided, in the recited order, with layers consisting of aluminum (layer thickness for specimen 10: 1 μm, for specimen 11: 2 μm, and for specimen 12: 3 μm), and aluminum oxide.

Specimen 13: a dry magnet body was provided, in the recited order, with layers consisting of aluminum and aluminum oxide. The aluminum layer thickness was 1 μm, and the aluminum oxide layer thickness was 17 μm. The aluminum oxide was applied by electroplating.

TABLE 1

| Specimen # | | Time t until failure | | | |
|---|---|---|---|---|---|
| | | | 2 days ≤ | 40 days ≤ | |
| invention | comparative | t < 2 days | t < 40 days | t < 70 days | t ≥ 70 days |
| 1 | | | | | x |
| 2 | | | | | x |
| 3 | | | | | x |
| 4 | | | | | x |
| 5 | | | | | x |
| 6 | | | | | x |
| | 7 | | x | | |
| | 8 | | x | | |
| | 9 | | | | x |
| | 10 | x | | | |
| | 11 | x | | | |
| | 12 | x | | | |
| | 13 | x | | | |

Test results of coated $Nd_2Fe_{14}B$ magnets in 0.9% NaCl solution at 60° C.
Magnet fails when coating lifts or buckling reaches 0.1 mm.
Magnets pass the test when time until failure is at least 70 days.
A magnet is corrosion resistant in terms of this invention when it passes the test, i.e. time until failure is at least 70 days.

Specimen samples 10 to 12, each having a composite coating consisting of an aluminum layer and an aluminum oxide layer (applied by ALD), but without an organic layer, all survived more than 1 day, but fewer than 2 days.

Specimen sample 13, also having a very thick aluminum oxide layer, failed within fewer than 24 hours. Specimen sample 13 appeared to be intact after 12 hours.

Specimen samples 7, 8, and 9 had composite coatings consisting of an aluminum layer, a Parylene C layer and an adhesion promoter therebetween. Specimen sample 7 having an aluminum layer thickness of 1 μm failed after 9 days, specimen sample 8 having an aluminum layer thickness of 2 μm failed after 36 days, and specimen sample 9 having an aluminum layer thickness of 3 μm passed the test, but some buckling was visible.

Specimen samples 1, 2, and 3, each having a composite coating (single-layer structure) according to the present invention, the coating consisting of an aluminum layer, an aluminum oxide layer, a Parylene C layer, and an adhesion promotor therebetween, did not show any sign of corrosion after 70 days (then the test was stopped).

Specimen samples 4, 5, and 6, each having a composite coating according to the present invention, the coating having a first layer structure and a second layer structure, and each layer structure consisting of an inorganic layer, a linker layer on the inorganic layer, and an organic layer formed from Parylene C on the linker layer, behaved similar to specimen samples 1, 2, and 3. None of specimen samples 4, 5, and 6 showed any sign of corrosion at the time when the test was stopped, i.e. after 70 days.

The above test results provide a clear indication that a neodymium iron boron permanent magnet having a composite coating comprising a certain layer sequence, i.e. a first layer structure and optionally also a second layer structure, as described above, wherein at least one aluminum layer is applied by PVD, and at least one aluminum oxide layer is applied by ALD and has a thickness of at least 50 nm, has excellent corrosion resistance even under aggressive conditions, and may be advantageously used in an intravascular blood pump. The test results also indicate that the application method of the aluminum oxide layer influences the corrosion resistance. See specimen sample 13 as compared to specimen samples 10 to 12.

Likewise, the test results indicate that the thickness of the aluminum layer influences the corrosion resistance. This becomes evident when comparing specimen samples 7, 8, and 9.

Furthermore, it is evident that an aluminum layer, an aluminum oxide layer, a linker layer (an adhesion promotor) and a Parylene C layer must be present in combination in order to provide for optimum corrosion resistance.

In order to achieve optimum corrosion protection it is advisable to apply the inventive composite coating to the non-magnetized magnet bodies, and to magnetize the magnet bodies only after the coating has been applied.

Specimen samples 1, 2, 3, 4, 5, and 6 fulfilled the above conditions. Non-magnetized magnet bodies were coated with the inventive composite coating, and magnetized after application of the complete composite coating. As a result, specimen samples 1 to 6 did not show any coating lifting, and buckling was less than 0.1 mm in 0.9 weight % NaCl solution at 60° C. for at least 70 days. Therefore, specimen samples 1 to 6 are corrosion-resistant magnets, in the sense of this invention.

The invention claimed is:

1. A method for producing a corrosion-resistant permanent magnet, the method comprising:

providing a non-magnetized magnet body, forming a first layer structure on the magnet body by depositing an inorganic layer on surfaces of the magnet body, depositing a linker layer on the inorganic layer, and depositing a layer of poly(2-chloro-p-xylylene) on the linker layer, and optionally forming a second layer structure on the first layer structure by depositing an inorganic layer on the first layer structure, depositing a linker layer on the inorganic layer, and depositing a layer of poly(2-chloro-p-xylylene) on the linker layer, and magnetizing the magnet body, wherein depositing of the inorganic layer of the first layer structure either comprises depositing an aluminum layer on the magnet body, or comprises depositing an aluminum layer on the magnet body and an aluminum oxide layer on the aluminum layer, depositing of the inorganic layer of the second layer structure comprises depositing an aluminum layer on the first layer structure, or comprises depositing an aluminum oxide layer on the first layer structure, or comprises depositing an aluminum layer on the first layer structure and an aluminum oxide layer on the aluminum layer, at least one of the aluminum layers is deposited by a physical vapor deposition process, and at least one aluminum oxide layer is deposited by an atomic layer deposition process to a thickness of at least 50 nm.

2. The method of claim 1, wherein a linker layer is deposited on the first layer structure.

3. The method of claim 1, wherein an aluminum oxide layer is deposited as the inorganic layer of the second layer structure.

4. The method of claim 1, wherein the magnet body is one of sintered magnet body, a rare-earth metal iron boron permanent magnet, or is rod shaped with rounded edges.

5. The method of claim 1, wherein the aluminum oxide layer of the first layer structure and/or the second layer structure is formed from $AlX_3$ as a first precursor compound and $H_2O$ as a second precursor compound, with X representing lower alkyl groups, which may be the same or different, or representing a hydrogen atom and lower alkyl groups, which may be the same or different, or representing halogen atoms, which may be the same or different.

6. The method of claim 5, wherein $AlX_3$ is selected from the group consisting of trimethyl aluminum (TMA), triethyl aluminum (TEA), triisobutyl aluminum (TIBA), dimethyl aluminum (DMAIH) and $AlCl_3$.

7. The method of claim 1, wherein at least one of the linker layers is formed by applying a linker by physical vapor deposition using plasma, or by physical vapor deposition without using plasma, or from a solution.

8. The method of claim 1, wherein the linker of at least one of the linker layers comprises one of a silane or a silane having one of a thiol, phosphine or disulfide group.

9. The method of claim 1, wherein the layer of poly(2-chloro-p-xylylene) of the first layer structure and/or the second layer structure is formed by plasma deposition of dichloro[2.2]paracyclophane.

10. The method of claim 1, wherein the aluminum layers of the first layer structure and/or the second layer structure have a thickness of 0.5 μm to 15 μm.

11. The method of claim 1, wherein the linker is selected from 3-(2-pyridylethyl)thiopropyl trimethoxysilane, 3-(4-pyridylethyl)thiopropyl trimethoxysilane, and 2-(diphenylphosphino)ethyl triethoxysilane.

12. The method of claim 1, wherein the thickness of the aluminum oxide layer of the first layer structure and/or the second layer structure is 50 nm to 200 nm.

13. The method of claim 1, wherein a combined thickness of the aluminum layer and the aluminum oxide layer of the first layer structure and/or the second layer structure is in a range from 5 μm to 15 μm.

14. The method of claim 1, wherein the linker layer has a thickness in a range from 20 nm to 50 nm.

15. The method of claim 1, wherein the thickness of the layer formed from poly(2-chloro-p-xylylene) of the first layer structure and/or the second layer structure is in a range from 5 μm to 20 μm.

16. The method of claim 1, wherein the thickness of the composite coating is no more than 200 μm.

17. The method of claim 10, wherein the thickness of the aluminum layers of the first layer structure or the second layer structure is 1 μm to 10 μm.

18. The method of claim 10, wherein the thickness of the aluminum layers of the first layer structure or the second layer structure is 1 μm to 5 μm.

19. The method of claim 12, wherein the thickness of the aluminum oxide layer of the first layer structure and/or the second layer structure is 80 nm to 120 nm.

20. The method of claim 16, wherein the thickness of the composite coating is no more than about 50 μm.

* * * * *